US00PP27147P2

(12) United States Plant Patent
Cain

(10) Patent No.: US PP27,147 P2
(45) Date of Patent: Sep. 13, 2016

(54) GRAPEVINE 'IFG TWENTY-TWO'

(50) Latin Name: ***Vitis interspecific* hybrid**
Varietal Denomination: IFG Twenty-two

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 15 days.

(21) Appl. No.: 14/545,067

(22) Filed: Mar. 23, 2015

(51) Int. Cl.
*A01H 5/08* (2006.01)

(52) U.S. Cl.
USPC ..... Plt./205

(58) Field of Classification Search
USPC ..... Plt./205
See application file for complete search history.

*Primary Examiner* — Annette Para

(57) ABSTRACT

This invention is a new and distinct grapevine variety denominated 'IFG Twenty-two'. The new grapevine is characterized by producing small naturally seedless reddish black to black berries having round to slightly elliptic shape with a unique grape lollipop-like labrusca flavor.

1 Drawing Sheet

Latin name of the genus and species claimed: *Vitis interspecific* hybrid.

Variety denomination: 'IFG Twenty-two'.

BACKGROUND OF THE INVENTION

The new and distinct grapevine described and claimed herein originated from a hand pollinated cross of the 01161-040-184 (unnamed *Vitis vinifera* selection from the IFG breeding program) and the 04025-037-112 (unnamed *Vitis interspecific* hybrid selection from the IFG breeding program) hybridized in May 2008. The abortive seed traces were subsequently embryo cultured and the resulting population of plants was planted in the field in April 2009. The present variety of grapevine was selected as a single plant in September 2010 and was first asexually propagated by hardwood cuttings in December 2010 near Delano, Kern County, Calif. The resulting propagules were planted during April 2011 near Delano, Kern County, Calif. and were found to reproduce true-to-type through at least one generation of asexual reproduction.

BRIEF SUMMARY OF THE INVENTION

The new gapevine 'IFG Twenty-two' is characterized by producing small naturally seedless reddish black to black berries having round to slightly elliptic shape with a unique grape lollipop-like labrusca flavor. The strong fruity flavor is reminiscent of grape lollipops. Fruits are medium in acidity, with dense, firm texture and remain firm even at very high sugar levels, often as high as 25 to 30 brix. Berries color readily even in hot climatic conditions and produce completely colored reddish black to black berries. Vines are very productive and can be pruned to short spurs. Clusters are large, and require tipping, thinning and sizing with gibberellic acid to enlarge berry size. The new grapevine differs from its maternal parent the 01161-040-184 selection by having slightly smaller berries which have a very distinct labrusca flavor as opposed to the neutral typical Vinifera flavor of 01161-040-184. 'IFG Twenty-two' has smaller, softer, less noticeable seed traces than its maternal parent. 'IFG Twenty-two' can be distinguished from its pollen parent, 04025-037-112, by having firmer, more dense flesh, as opposed to the very soft flesh of 04025-037-112; by having a slightly more elliptical berry shape; by having a slightly more purple color as opposed to the more black color of 04025-037-112, and by having a grape lollipop-like labrusca flavor rather than a Concord-like flavor of 04025-037-112.

Grape breeders have used several native American grape species to improve hardiness, disease and insect resistance as well as incorporate aromatic flavors into the vinifera species. Previously introduced interspecific varieties have had very limited commercial success due to small fruit size, large seed traces, slipskin texture or lack of firmness. The new grapevine variety is being introduced because of its unique grape lollipop-like flavor combined with firm texture, seedlessness, good adhesion of skin and flesh and excellent coloring characteristics.

BRIEF DESCRIPTION OF THE FIGURE

The accompanying photographic illustration in FIG. 1 illustrates in full color 'IFG Twenty-two'. The photograph was taken outdoors with indirect lighting. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*vitis* spp.) (1983) which was developed in collaboration with the Office International de la Vigne et du Vin (OIV) and the International Union for the Protection of New Varieties of Plants (UPOV).

The descriptive matter which follows pertains to 'IFG Twenty-two' plants grown in the vicinity of Delano, Kern County, Calif. during 2013 and 2014, and is believed to apply to plants of the variety grown under similar conditions of soil and climate elsewhere:

VINE

General:

*Size*.—Medium.
*Vigor*.—Medium.
*Density of foliage*.—Medium.
*Productivity*.—Very productive.
*Root stock*.—Own root.
*Training method*.—Typically spur pruned leaving 2 bud spurs.

Trunk:

*Trunk diameter of* 4-*year-old vines at* 30 *cm above the soil line*.—About 4.3 cm.
*Shape*.—Medium.
*Straps*.—Short — split.
*Surface texture*.—Shaggy.
*Inner bark color*.—Can be any of the following colors; Greyed-orange; 177A and B and C.

SHOOTS

Young shoot:

*Form of tip*.—Wide open.
*Distribution of anthocyanin coloration of tip*.—Absent.
*Intensity of anthocyanin coloration of tip*.—Absent.
*Density of prostrate hairs of tip*.—Sparse.
*Density of erect hairs of tip*.—Absent to very sparse.
*Color*.—Can be any of the following colors; Yellow-green; N144A and C.

Woody shoot (mature canes):

*Shape*.—Stocky to medium.
*Internode length*.—Medium; About 16 cm.
*Width at node*.—About 1.5 cm.
*Cross section*.—Elliptic.
*Surface*.—Striate.
*Main color*.—Can be any of the following colors; Greyed-orange; 164B and C and 165A and B and C.
*Density of erect hairs of nodes*.—None.
*Density of erect hairs on internodes*.—None.
*Growth of axillary shoots*.—Medium ; Approximately 11.3 cm.

Flowering shoot:

*Vigor during flowering*.—Medium.
*Attitude during flowering on shoots not tied*.—Semi-erect to Horizontal.
*Color*.—Dorsal side of internodes — Green with Red stripes.
*Color*.—Ventral side of internodes — Green with Red stripes.
*Color*.—Dorsal side of nodes — Green.
*Color*.—Ventral side of nodes — Green.
*Density of prostrate hairs of nodes*.—Sparse.
*Density of erect hairs of nodes*.—None.
*Density of prostrate hairs on internode*.—Very sparse.
*Density of erect hairs on internode*.—None.
*Anthocyanin coloration of buds*.—Absent.

Tendrils:

*Distribution on the shoot* (*at full flowering*).—Discontinuous.
*Length of tendril*.—Long; About 30.4 cm.
*Thickness*.—Thin.
*Color*.—Yellow-green; N144A.
*Form*.—Trifurcated.
*Number of consecutive tendrils*.—2.

LEAVES

Young leaves:

*Color of upper surface of first four distal unfolded leaves*.—Yellow-green; 144A.
*Average intensity of anthocyanin coloration of six distal leaves prior to flowering*.—Absent or very weak.
*Density of prostrate hairs between veins* (*lower surface*).—Very sparse.
*Density of prostrate hairs on veins* (*lower surface*).—Very sparse.
*Density of erect hairs between veins* (*lower surface*).—Absent.
*Density of erect hairs on veins* (*lower surface*).—Very sparse.

Mature leaves:

*Average length*.—About 12.2 cm.
*Average width*.—About 11 cm.
*Mature leaf size*.—Small.
*Shape of blade*.—Pentagonal.
*Number of lobes*.—5.
*Anthocyanin coloration of main veins on upper side of blade*.—Absent.
*Mature leaf profile*.—Undulate.
*Blistering surface of blade upper surface*.—Absent to very weak.
*Leaf blade tip*.—In the plane of the leaf.
*Undulation of margin*.—Medium.
*Thickness*.—Medium.
*Undulation of blade between main and lateral veins*.—Overall.
*Shape of teeth*.—Mixture of both sides straight and both sides concave.
*Length of teeth*.—Long.
*Ratio length/width of teeth*.—Medium.
*Shape of upper lateral sinuses*.—Lobes slightly to strongly overlapping.
*Depth of upper lateral sinuses*.—Deep.
*General shape of petiole sinus*.—Half open.
*Shape of base of upper leaf sinuses*.—U-shaped.
*Tooth at petiole sinus*.—Absent.
*Density of prostrate hairs between veins on lower surface of blade*.—Very sparse.
*Density of erect hairs between veins on lower surface of blade*.—Absent.
*Density of prostrate hairs on main veins on lower surface of blade*.—Sparse.
*Density of erect hairs on main veins on lower surface of blade*.—Very sparse.
*Density of prostrate hairs on main veins on upper surface of blade*.—Very sparse.
*Density of erect hairs on main veins on upper surface of blade*.—None.
*Autumn coloration of leaves*.—Leaves can be a single color or combination of colors, in a mottled pattern or on the edges of the leaves; Yellow 11A, and Greyed- Yellow; 162A and B, and Orange-red; N34A, and Greyed-red; 181A, and Greyed-purple; 187A and B.

Upper surface:

*Color*.—Can be any of the following colors; Green; 137A and B.

*Anthocyanin coloration of main veins*.—Absent.

*Surface appearance*.—Semi-glossy.

*Blistering surface of blade*.—Very weak.

Lower surface:

*Color*.—Can be any of the following colors; Yellow-green; 146A and B and C.

*Anthocyanin coloration of main veins* (*lower surface*).—Absent.

*Glossiness*.—Weak.

*Surface texture*.—Smooth.

*Surface appearance*.—Dull.

Petiole:

*Length*.—About 11.0 cm.

*Length of petiole compared to middle vein*.—Slightly shorter.

*Density of prostrate hairs on petiole*.—Very sparse.

*Density of erect hairs on petiole*.—None.

Buds:

*Bud fruitfulness*.—Basal: Mostly fruitful.

*Position of first fruitful shoot on previous season cane*.—$1^{st}$ to $2^{nd}$ node.

*Time of bud burst*.—Mid-season; Mar. 7, 2014.

FLOWERS

General:

*Flower sex*.—Hermaphrodite.

*Length of first inflorescence*.—Medium; About 16.7 cm long by 9.9 cm wide.

*Position of first flowering and fruiting node*.—$4^{th}$ to $5^{th}$ node (current season growth).

*Number of inflorescence per flowering shoot*.—1.1 to 2; About 1.3.

*Time of bloom*.—Medium to late as compared with similar varieties in the growing area of Delano, Calif.

*Date of full bloom*.—May 3, 2014.

FRUIT

General:

*Ripening period*.—Early; Approximately Jul. 23, 2014.

*Use*.—Fresh market.

*Keeping quality*.—Good.

*Resistance to*.—Insects: Average typical of *Vitis vinifera* species. Diseases: Average typical of *Vitis vinifera* species.

*Refractometer test*.—Solid-sugar: About 20.4 Brix.

*Brix/acid*.—*About* 42.5.

*Titratable acidity*.—About 0.48.

*Juice pH*.—About 3.64.

Cluster:

*Mature cluster length* (*peduncle excluded*).—About 33.2 cm.

*Mature cluster width*.—About 18.4 cm.

*Mature cluster weight*.—About 943 g.

*Bunch density*.—Medium to somewhat dense.

*Number of berries*.—About 348.

*Form*.—Conical.

Peduncle:

*Lignification of peduncle*.—Weak.

*Length of peduncle*.—Medium-long; Approximately 6.3 cm.

Berry:

*Uniformity of size*.—Uniform.

*Single berry weight*.—About 3.5 g natural; to about 5.2 g when treated with gibberellic acid.

*Shape*.—Round to slightly elliptic.

*Seeds*.—Contains small rudimentary seed traces that are occasionally noticeable.

*Cross section*.—Circular.

*Berry dimensions*.—Longitudinal axis: About 1.9 cm. Horizontal axis: About 1.7 cm.

*Berry firmness*.—Medium to firm.

*Particular flavor*.—Labrusca (similar to grape flavored candy).

*Bloom* (*cuticular wax*).—Medium.

*Berry separation from pedicel*.—Difficult.

*Skin color* (*without bloom*).—Can be any of the following colors; Greyed-purple; N186A and B.

Skin:

*Thickness*.—Medium.

*Texture*.—Medium tough.

*Reticulation*.—Absent.

*Tenacity*.—Tenacious to flesh.

What is claimed:

1. A new and distinct variety of grapevine as herein illustrated and described.

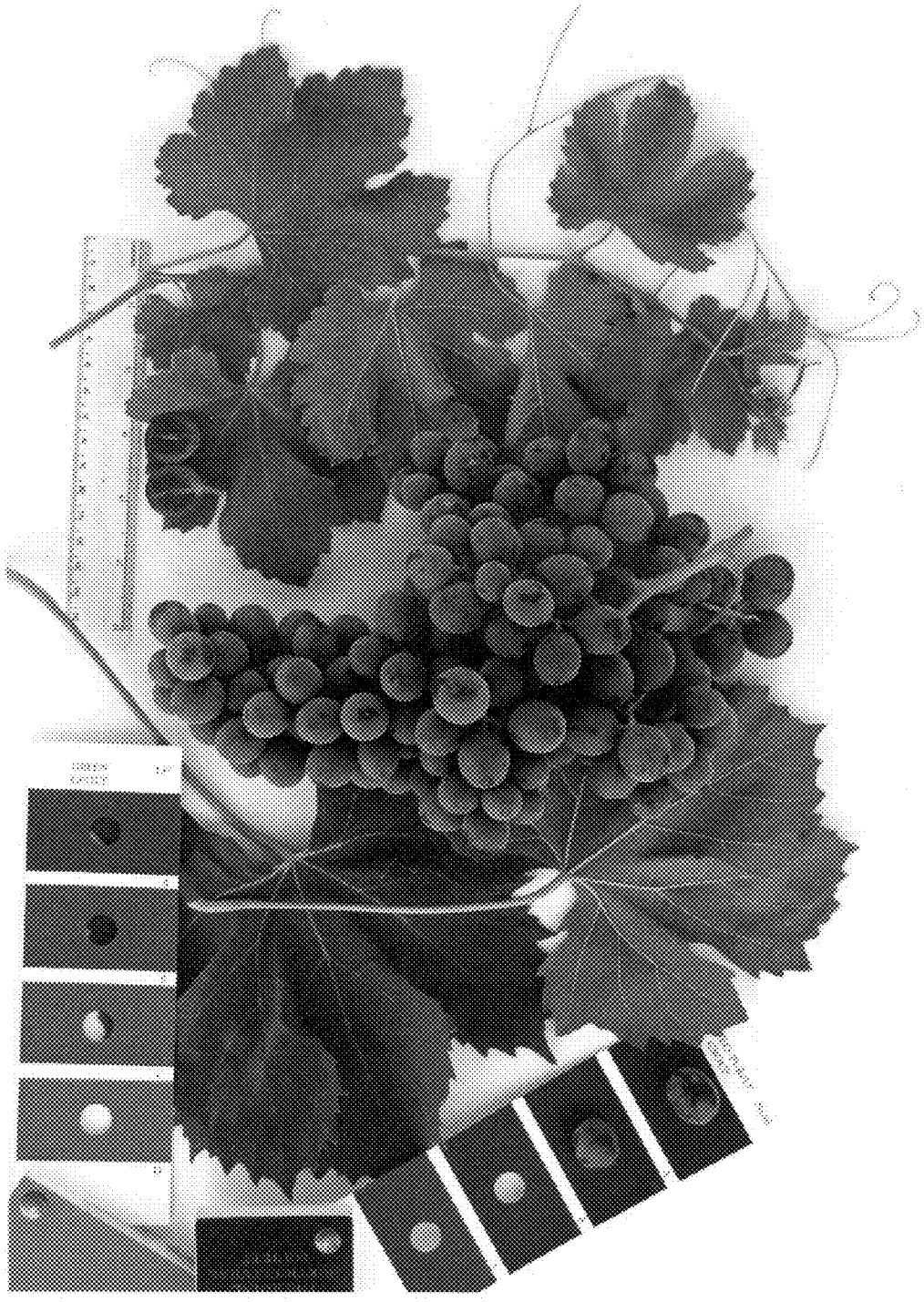

* * * * *